(12) United States Patent
Jeanne et al.

(10) Patent No.: US 10,987,030 B2
(45) Date of Patent: Apr. 27, 2021

(54) METHOD AND APPARATUS FOR FACE DETECTION/RECOGNITION SYSTEMS

(71) Applicant: KONINKLIJKE PHILIPS N.V., Eindhoven (NL)

(72) Inventors: Vincent Jeanne, Migne Auxances (FR); Solene Moreau, Plougonvelin (FR); Michel Jozef Agnes Asselman, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 146 days.

(21) Appl. No.: 16/310,382

(22) PCT Filed: Jun. 29, 2017

(86) PCT No.: PCT/EP2017/066219
§ 371 (c)(1),
(2) Date: Dec. 14, 2018

(87) PCT Pub. No.: WO2018/002275
PCT Pub. Date: Jan. 4, 2018

(65) Prior Publication Data
US 2019/0209052 A1    Jul. 11, 2019

(30) Foreign Application Priority Data

Jun. 30, 2016  (EP) ..................... 16305819

(51) Int. Cl.
*A61B 5/1171*    (2016.01)
*A61B 5/00*    (2006.01)
(Continued)

(52) U.S. Cl.
CPC .......... *A61B 5/1176* (2013.01); *A61B 5/0064* (2013.01); *A61B 5/0205* (2013.01);
(Continued)

(58) Field of Classification Search
None
See application file for complete search history.

(56) References Cited

U.S. PATENT DOCUMENTS 7,643,659 B2 *  1/2010  Cao .................... G06K 9/00604
                                                      382/118
9,396,382 B2 *  7/2016  Troy .................. G06K 9/00093
(Continued)

FOREIGN PATENT DOCUMENTS

WO    2013187999 A1   12/2013
WO    2015095760 A1    6/2015

OTHER PUBLICATIONS

Kollreider, et al., "Evaluating Liveness by Face Images and the Structure Tensor", Automatic Identification Advanced Technologies, 2005, Fourth IEEE Work Shop on Buffalo, NY, Oct. 17, 2005, pp. 75-80.
(Continued)

*Primary Examiner* — Anand P Bhatnagar

(57) ABSTRACT

A computer implemented method for detecting an attempt to spoof and facial recognitions apparatus determines for a plurality of spatially separated regions of a surface, a respective measure of at least one vital sign. A determination is made from the respective measures of at least one vital sign, homogeneity information associated with the respective measures, the homogeneity information is used to determine if said spatially separate regions of said surface are living tissue.

14 Claims, 7 Drawing Sheets

(51) Int. Cl.
*G06K 9/00* (2006.01)
*A61B 5/024* (2006.01)
*A61B 5/0205* (2006.01)
*A61B 5/08* (2006.01)
*A61B 5/1455* (2006.01)
*A61B 5/145* (2006.01)

(52) U.S. Cl.
CPC ........ *A61B 5/02416* (2013.01); *A61B 5/7221* (2013.01); *A61B 5/7246* (2013.01); *G06K 9/00228* (2013.01); *G06K 9/00241* (2013.01); *G06K 9/00899* (2013.01); *G06K 9/00906* (2013.01); *A61B 5/0077* (2013.01); *A61B 5/02433* (2013.01); *A61B 5/0816* (2013.01); *A61B 5/1455* (2013.01); *A61B 5/14535* (2013.01); *A61B 5/14551* (2013.01); *G06K 2009/00939* (2013.01)

(56) References Cited

U.S. PATENT DOCUMENTS

| | | | | |
|---|---|---|---|---|
| 9,665,784 | B2* | 5/2017 | Derakhshani | A61B 5/6898 |
| 9,697,414 | B2* | 7/2017 | Baldwin | G06K 9/00228 |
| 9,898,674 | B2* | 2/2018 | Connell, II | G06K 9/00912 |
| 10,242,249 | B2* | 3/2019 | Kim | G06K 9/6207 |
| 10,441,198 | B2* | 10/2019 | Matsuo | G06K 9/00536 |
| 2007/0154096 | A1* | 7/2007 | Cao | G06K 9/00234 382/190 |
| 2010/0034433 | A1 | 2/2010 | Thiebot et al. | |
| 2012/0321145 | A1* | 12/2012 | Saito | G06F 16/5838 382/118 |
| 2014/0276099 | A1 | 9/2014 | Kirenko et al. | |
| 2015/0148681 | A1* | 5/2015 | Abreu | A61B 5/01 600/474 |
| 2015/0150453 | A1* | 6/2015 | Abreu | A61B 5/0075 600/474 |
| 2015/0186711 | A1* | 7/2015 | Baldwin | G06F 21/32 382/118 |
| 2015/0236740 | A1* | 8/2015 | De Haan | A61B 5/6887 375/340 |

OTHER PUBLICATIONS

Kollreider, et al., "Non-intrusive liveness detection by face images", Science Direct, Image and Vision Computing 27 (2009) pp. 233-244.
Duc, et al., "Your face is Not your password—Face Authentication ByPassing", pp. 1-16.
Viola, P., et al., "Rapid Object Detection Using a Boosted Cascade of Simple Features", Mitsubishi Electric Research Laboratories, Accepted Conference on Computer Vision and Pattern Recognition 2001, pp. 1-9.
Choudhury, et al., "Three-Dimensional Face Recognition Using Shape Codes Extracted From Projected Structured Light Patterns", pp. 161-166. (Abstract).
Shahid, A., "Young Asian man boards Air Canada flight from Hong Kong to Vancouver disguised as old man: photos", Daily News Staff Writer, Friday, Nov. 5, 2010, 6 pages.
Schneiderman, H., "A Statistical Approach to 3D Object Detection Applied to Faces and Cars", May 10, 2000, Robotics Institute Carnegie Mellon University, Pittsbury, PA, 106 pages.
Tan, et al., "Face Liveness Detection from a Single Image with Sparse Low Rank Bilinear Discriminative Model", pp. 1-14. (Abstract).
Rowley, H., "Neural Network-Based Face Detection", May 1999, School of Computer Science, Computer Science Department, Carnegie Mellon University, Thesis, 149 pages.
Hague, et al., Can Contact-Free Measurements of Heartbeat Signal Be Used in Forensics?, 23rd European Signal Processing Conference, 2015 IEEE, pp. 774-778.
Yan, et al., "Face Liveness Detection by Exploring Multiple Scenic Clues", 6 pages (Abstract).

* cited by examiner

METHOD AND APPARATUS FOR FACE DETECTION/RECOGNITION SYSTEMS

CROSS-REFERENCE TO PRIOR APPLICATIONS

This application is the U.S. National Phase application under 35 U.S.C. § 371 of International Application No. PCT/EP2017/066219, filed on Jun. 29, 2017, which claims the benefit of European Application Serial No. 16305819.1, filed Jun. 30, 2016. These applications are hereby incorporated by reference herein, for all purposes.

FIELD

Some embodiments relate to a method and apparatus for use in particular but not exclusively in face detection/recognition systems.

BACKGROUND

In an effort to increase security, facial recognition is being used more and more in various types of applications. The expected added value of facial recognition is the increased prevention of counterfeiting.

For example, cameras are frequently used in security systems such as surveillance equipment and more and more they are used to photograph or film people for identification and logging purposes as they pass through check-points such as passport controls or entries to secure areas.

Current face-recognition systems have difficulty in detecting where a subject is a photograph of another person or where a subject is wearing a mask. The act of a subject generating false positive from a face recognition system in this manner is known as "spoofing".

Spoofing is problem enough for situations where there is human intervention and the camera is just for logging purposes because the mask will often be detected by the security personnel and the only error will be in the log files. Showing a printed image will not work in this situation. That said, sometimes people wearing masks could slip through completely undetected. In a situation where access were to be granted automatically by a face recognition system, or where the security person is on the other side of the camera, this is a problem as no-one is there to see the person in the flesh and so artificial representations of a human face can work. For example, a wearable active display like a computer tablet may be used.

Therefore it is desirable to reduce the reliance on the presence of security personnel and provide a way of detecting the spoofing attempt using the camera system itself.

There may also be less critical situations where it remains desirable to reduce the opportunity for fooling a camera system by the use of a mask.

SUMMARY

According to one aspect, there is provided a computer implemented method comprising: determining for a plurality of spatially separated regions of a surface, a respective measure of at least one vital sign; determining from said respective measures of at least one vital sign, homogeneity information associated with said respective measures; and using said homogeneity information to determine if said spatially separate regions of said surface are living tissue.

The method may comprise identifying a face area in a sequence of video frames, at least one of said spatially separated regions being positioned in said face area, said surface comprising at least partially said face area. This may be advantageous as it allows the system to check across multiple regions of a face, ensuring that a spoofer is not wearing a partial mask.

The respective measure of at least one vital sign may comprise a heart-beat signal, the method may further comprise extracting, from the sequence of video frames, a heart-beat signal for each of the spatially separated regions so as to obtain a plurality of heart-beat signals. This may be advantageous as it allows the system to check whether the face is made of living tissue.

The method may comprise determining the homogeneity information by comparing the heart-beat signals. This may be advantageous as it allows the system to compare the measured values across a face, minimising the ability of a spoofer to trick the system by simulating a heart-beat.

The use of the homogeneity information, may comprise comparing the homogeneity information against a limit. The limit may be a pre-set value. This may be advantageous as it allows the system to check the values measured against those previously given to the system. This may give an operator an ability to tune the system to be more or less sensitive to a potential spoofers.

The homogeneity information may be determined by extracting a heart-rate from the heart-beat signals and combining the heart-rates from a plurality of the spatially separate regions and determining at least one of a standard deviation and a maximum value of the combined heart-rates. The maximum value may be the maximum value of a histogram distribution. This may be advantageous as it may allow the system to check for homogeneity across different areas of the face, which may further the ability of the system to detect a partial mask.

The determining of the homogeneity information, may comprise finding a correlation between at least one pair of the heart-beat signals.

The determining of the homogeneity information may comprise extracting heart-rates for a spatially separate region from a plurality of time segments and determining a standard deviation of the heart-rates extracted from each time segment.

The method may comprise determining a colour vector for a spatially separate region for each of a plurality of time segments and determining variations of the colour vectors over the plurality of time segments. This may be advantageous as it allows the system to, for example, calculate the HR-related colour variation (HR-axis) to increase the system's ability to detect a spoofed face.

The colour vector for the spatially separate region for each of a plurality of time segments may be obtained from a haemoglobin absorption spectrum.

The method may comprise determining an area in the sequence of video frames where respiration is measurable, extracting a respiration signal and extracting a correlation between said respiration signal and heart-beat signal and comparing the correlation to a limit. This may be advantageous, as it allows the system to use a different photoplethysmographic (PPG) waveform which a spoofed face may not possess.

According to another aspect there is provided a method of preparing a spoofing detection unit comprising performing a teaching procedure, the teaching procedure comprising performing any of the methods above on a video sequence containing images of a real face using first homogeneity information, performing any of the above method on a video sequence containing images of a spoof face using second homogeneity information, and setting a limit to a value lying between the first and second homogeneity information.

According to another aspect there is provided a spoofing detection apparatus comprising at least one processor configured to: determine for a plurality of spatially separated regions of a surface, a respective measure of at least one vital sign; determine from said respective measures of said at least one vital sign, homogeneity information associated with said respective measures; and use said homogeneity information to determine if said spatially separate regions of said surface are living tissue.

The apparatus may comprise an input to receive a sequence of video frames and the at least one processor may be configured to identify a face area in a sequence of video frames, to identify a set of spatially separate skin portions in the face area, and to extract a heart-beat signal for each of the spatially separate skin portions and from each heart-beat signal, to extract a heart-rate.

The at least one processor may be configured to calculate a valid vital sign metric and compare the valid vital sign metric against a limit to decide if the sequence of video frames containing the face area has been captured directly from the face of a living person.

The at least one processor may be configured to identify a face area in a sequence of video frames, at least one of said spatially separated regions being positioned in said face area, said surface comprising at least partially said face area.

The respective measure of at least one vital sign may comprise a heart-beat signal, the at least one processor may be configured to extract, from the sequence of video frames, a heart-beat signal for each of the spatially separated regions so as to obtain a plurality of heart-beat signals.

The at least one processor may be configured to determine the homogeneity information by comparing the heart-beat signals.

The at least one processor may be configured to compare the homogeneity information against a limit.

The at least one processor may be configured to determine the homogeneity information by extracting a heart-rate from the heart-beat signals, combining the heart-rates from a plurality of the spatially separate regions, and determining at least one of a standard deviation and a maximum value of the combined heart-rates. The maximum value may be the maximum value of a histogram distribution.

The at least one processor may be configured to find a correlation between at least one pair of the heart-beat signals.

The at least one processor may be configured to extract heart-rates for a spatially separate region from a plurality of time segments and determine a standard deviation of the heart-rates extracted from each time segment.

The at least one processor may be configured to determine a colour vector for a spatially separate region for each of a plurality of time segments and to determine variations of the colour vectors over the plurality of time segments.

The colour vector for the spatially separate region for each of a plurality of time segments may be obtained from a haemoglobin absorption spectrum.

The at least one processor may be configured to determine an area in the sequence of video frames where respiration is measurable, extract a respiration signal, extract a correlation between said respiration signal and heart-beat signal, and compare the correlation to a limit.

According to another aspect there is provided a visual recognition system which may comprise: a video camera operable to capture a sequence of video frames; a spoofing detection apparatus as previously described, and an alert unit configured to generate an alert if a spoofing attempt is detected.

According to another aspect, there is provided a method for detecting an attempt to fool a visual recognition system comprising: identifying a face area in a sequence of video frames; identifying a plurality of spatially separate skin portions, at least one skin portion being positioned in the face area; extracting, from the sequence of video frames, a heart-beat signal for each of the spatially separate skin portions so as to obtain a plurality of heart-beat signals, each heart-beat signal being a member; calculating a valid vital sign metric from a heart beat signal by performing a comparison between members of the plurality; comparing the valid vital sign metric against a limit to decide if the video sequence containing the face area has been captured directly from a living person.

According to some aspects, there is provided a program product comprising a computer-readable storage device including a computer-readable program for providing a computer-implemented game, wherein the computer-readable program when executed on a computer causes the computer to perform any one or more of the method steps described previously.

A computer program comprising program code means adapted to perform the method(s) may also be provided. The computer program may be stored and/or otherwise embodied by means of a carrier medium.

In the above, many different embodiments have been described. It should be appreciated that further embodiments may be provided by the combination of any two or more of the embodiments described above.

Various other aspects and further embodiments are also described in the following detailed description and in the attached claims.

BRIEF DESCRIPTION OF THE DRAWINGS

The above, as well as additional objects, features and advantages of the disclosed devices, systems and methods, will be better understood through the following illustrative and non-limiting detailed description of embodiments of devices and methods, with reference to the appended drawings, in which.

DETAILED DESCRIPTION OF EMBODIMENTS

Figure 1:
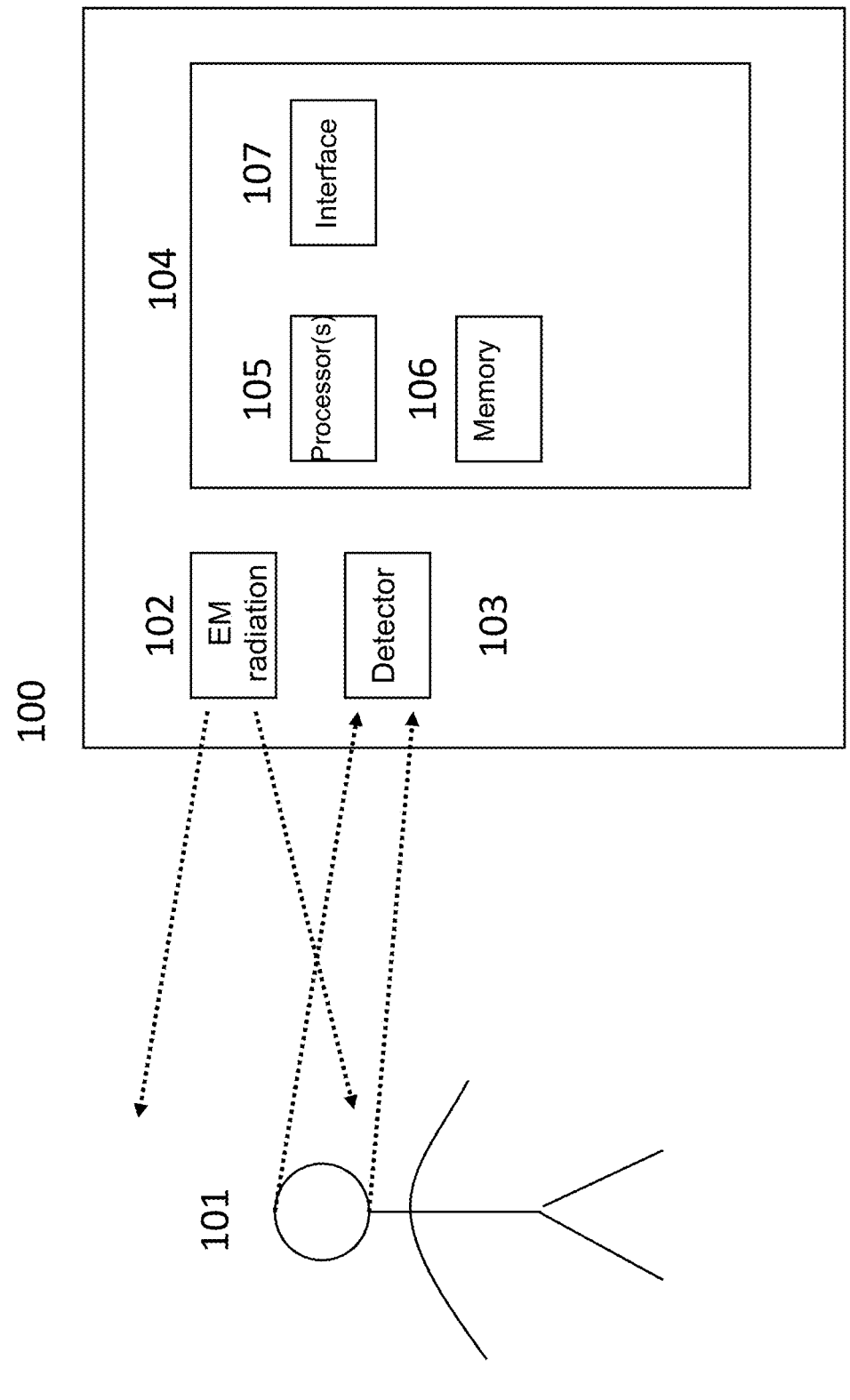
FIG. 1 shows a system of some embodiments.

Some embodiments provide a computer implemented method comprising: determining for a plurality of spatially separated regions of a surface, a respective measure of at least one vital sign; determining from said respective measures of at least one vital sign, homogeneity information associated with said respective measures; and using said homogeneity information to determine if said spatially separate regions of said surface are living tissue. This may be advantageous as it may remove the need for a person to be present during the digital identification process, by utilising a detected vital sign of a person attempting to pass the facial recognition system. Embodiments may also allow the system to check whether a person is wearing a partial mask, wherein the wearer has some of their face exposed.

In the following description, the same references designate like elements.

Some embodiments relate to a method and apparatus for an improved biometric identifier for face detection/recognition systems by utilizing human vital sign signals from a plurality of areas of a face.

Some embodiments utilize the presence of photoplethysmographic (PPG) waveforms caused by heart pulsation to determine if the face of a subject analysed by a facial recognition/detection system is that of a real face. Photoplethysmography (PPG) is an optical method involving the extraction of a signal indicative of a physiological process or vital sign from a subject. The vital signs may be obtained by the face detection system though a sequence of images. This allows the face detection system to ascertain whether the face being imaged is real or a spoof (a photograph or a mask).

In some embodiments a simple approach may be to qualify a face as real if a photoplethysmographic waveform can be detected. In some scenarios this method may not be sufficient because a subject may use parts of a face picture (e.g. the eyes), or part of a mask in conjunction with parts of their own face to spoof the recognition/detection system.

Some embodiments may use an approach involving spatially resolved photoplethysmographic waveforms in combinations with a homogeneity measure to qualify a detected face as real or not. As the same photoplethysmographic pulse waveform is homogeneously distributed across the face being measured, utilizing spatially resolved photoplethysmographic waveforms may aid in the correct identification of a face as being real.

In some embodiments a check for consistency in the pulse waveforms over time may be determined. Such checks may further reduce the possibility of counterfeiting the detection/recognition system.

The method may comprise identifying a face area in a sequence of video frames, at least one of said spatially separated regions being positioned in said face area, said surface comprising at least partially said face area. This may be advantageous as it allows the system to check across multiple regions of a face, ensuring that a spoofer is not wearing a partial mask.

The respective measure of at least one vital sign may comprise a heart-beat signal, the method may further comprise extracting, from the sequence of video frames, a heart-beat signal for each of the spatially separated regions so as to obtain a plurality of heart-beat signals. This may be advantageous as it allows the system to check whether the face is made of living tissue.

Some embodiments identify the face region of a subject in a series of frames through the capture of a video stream. Some embodiments may then identify separate sub-regions in the face of a subject from which multiple photoplethysmography (PPG) streams may be extracted. The homogeneity of these multiple waveforms may then be calculated. For example, heart-rates (HRs) may be extracted and checked for consistency over time. The results of these checks may then be utilized to determine if the face of a subject is real.

In some embodiments, the method for an improved biometric identifier for face detection/recognition system may comprise:
    identifying a face area in a sequence of video frames;
    identifying a set of spatially separate portions in the face area;
    extracting a heart-beat signal for each of the portions;
    comparing the extracted signals and calculating a homogeneity metric; and
    comparing the similarity metric against a limit to decide if the face is real.

The method may comprise determining the homogeneity information by comparing the heart-beat signals. This may be advantageous as it allows the system to compare the measured values across a face, minimising the ability of a spoofer to trick the system by simulating a heart-beat.

The use of the homogeneity information, may comprise comparing the homogeneity information against a limit. The limit may be a pre-set value. This may be advantageous as it allows the system to check the values measured against those previously given to the system. This may give an operator an ability to tune the system to be more or less sensitive to a potential spoofers.

The homogeneity information may be determined by extracting a heart-rate from the heart-beat signals and combining the heart-rates from a plurality of the spatially separate regions and determining at least one of a standard deviation and a maximum value of the combined heart-rates. The maximum value may be the maximum value of a histogram distribution. This may be advantageous as it may allow the system to check for homogeneity across different areas of the face, which may further the ability of the system to detect a partial mask.

The determining of the homogeneity information, may comprise finding a correlation between at least one pair of the heart-beat signals.

The determining of the homogeneity information may comprise extracting heart-rates for a spatially separate region from a plurality of time segments and determining a standard deviation of the heart-rates extracted from each time segment.

In some embodiments, options to check the homogeneity of the photoplethysmography (PPG) waveforms may comprise one or more of:
    the standard deviation of heat-rates;
    the maximum of a histogram of the heart-rates;
    the correlation of heart-rates;
    the standard deviation of variations in heart-rate over time segments; and
    the average distance of heart-rate related colour vector variations over time.

The method may comprise determining a colour vector for a spatially separate region for each of a plurality of time segments and determining variations of the colour vectors over the plurality of time segments. This may be advantageous as it allows the system to, for example, calculate the HR-related colour variation (HR-axis) to increase the system's ability to detect a spoofed face.

The colour vector for the spatially separate region for each of a plurality of time segments may be obtained from a haemoglobin absorption spectrum.

In some embodiments the average distance of heart-rate related colour vector may be Euclidean. In other embodiments the temporal variation in an observed light spectrum may not be consistent over time and/or it may differ considerably from the expected heart-rate-induced variation of light spectrum, based on the absorption spectrum of haemoglobin.

The homogeneity of the photoplethysmography (PPG) waveforms may be measured using one or more of these options in any combination. In some embodiments all of the above options are used. In other embodiments the options involving temporal segmenting are preferentially used in combination.

In some embodiments the relative amplitudes, and shapes of the photoplethysmography (PPG) waveforms may be used.

In some embodiments controlled lighting may be utilized to illuminate the face of a subject in a uniform diffuse manner.

In some embodiments specular reflections may be reduced through the use of a source that is polarized, for example having a cross-polarizer on the camera lens. It should be appreciated that other types of polarization may be used.

In some embodiments the lighting may comprise infrared (IR) electromagnetic waves. Using infrared light may improve sensitivity and make the presence of the system and the running of a scan less obvious to a subject. It should be appreciated that other wavelengths of electromagnetic waves may be used in the alternative or additionally.

Some application may favour a particular type of radiation. For example automotive applications may favour IR radiation.

Certain physiological processes can be observed via skin reflectance variations. The human skin can be modelled as an object with at least two layers, one of those being the epidermis (a thin surface layer) and the other the dermis (a thicker layer underneath the epidermis). A certain percentage 5% of an incoming ray of light is reflected at the skin surface. The remaining light is scattered and absorbed within the two skin layers in a phenomenon known as body reflectance (described in the Dichromatic Reflection Model). The melanin, typically present at the boundary of epidermis and dermis, behaves like an optical filter, mainly absorbing light. In the dermis, light is both scattered and absorbed. The absorption is dependent on the blood composition, so that the absorption is sensitive to blood flow variations. The dermis contains a dense network of blood vessels, about 10% of an adult's total vessel network. These vessels contract and expand according of the blood flow in the body. They consequently change the structures of the dermis, which influences the reflectance of the skin layers.

It is possible to detect and extract signals which have some periodic content in these changes and from that obtain a result such as a frequency in the case of periodic processes. For example, a subject may be illuminated with light and filmed using a video camera. By analysing changes in the values of corresponding pixels between frames of the sequence of images, a time-variant signal can be extracted. This signal may be transformed into frequency-like domain using something like a Fast Fourier Transform and from the frequency-domain spectra, a value for the subject's heart-rate and/or respiration rate (rate of breathing) may be arrived at as a physiological measurement. These physiological measurements are often called vital signs. Any one or more vital signs may be used with embodiments. Any vital sign may be used in some embodiments.

The method may comprise determining an area in the sequence of video frames where respiration is measurable, extracting a respiration signal and extracting a correlation between said respiration signal and heart-beat signal and comparing the correlation to a limit. This may be advantageous, as it allows the system to use a different photoplethysmographic (PPG) waveform which a spoofed face may not possess.

In some embodiments a gating check on the illumination may be utilized, which may include an active illumination system where frames are consecutively acquired with and without active illumination. The gating check may be performed to remove the impact of ambient lighting. Before being analysed by the algorithm, the consecutive images (active light+ambient vs ambient light only) may be subtracted to use an image containing only the active light to improve the reliability of the system.

In some embodiments the relative phases of the photoplethysmography (PPG) waveforms may be checked. Checking the phases of the photoplethysmography (PPG) waveforms may improve the reliability of the system as the waveforms should be close in phase and well correlated.

Reference is now made to FIG. 1 which shows an embodiment of a face detection system 100 and a subject 101. The face detection system 100 comprises an electromagnetic radiation source 102. It should be appreciated that the electromagnetic radiation source 102 may emit any suitable wavelength of light or infrared, as previously mentioned. In some embodiments, the electromagnetic radiation 102 may be omitted and ambient light may be used. An electromagnetic radiation detector 103 is provided. It should be appreciated that the light electromagnetic radiation 103 may detect any suitable wavelength of light, dependent on the electromagnetic radiation source/ambient light.

In some embodiments, the electromagnetic radiation detector may be a camera. In some embodiments, the camera may be a video camera. It should be appreciated, that in other embodiments, any other suitable detector may be used.

The system comprises a signal processor 104. The signal processor may comprise at least one processor 105, at least one memory 106, and an interface 107. The interface is configured to receive the input images and to provide an output. Some of the types of output which may be provided by some embodiments will be described later.

Figure 4:
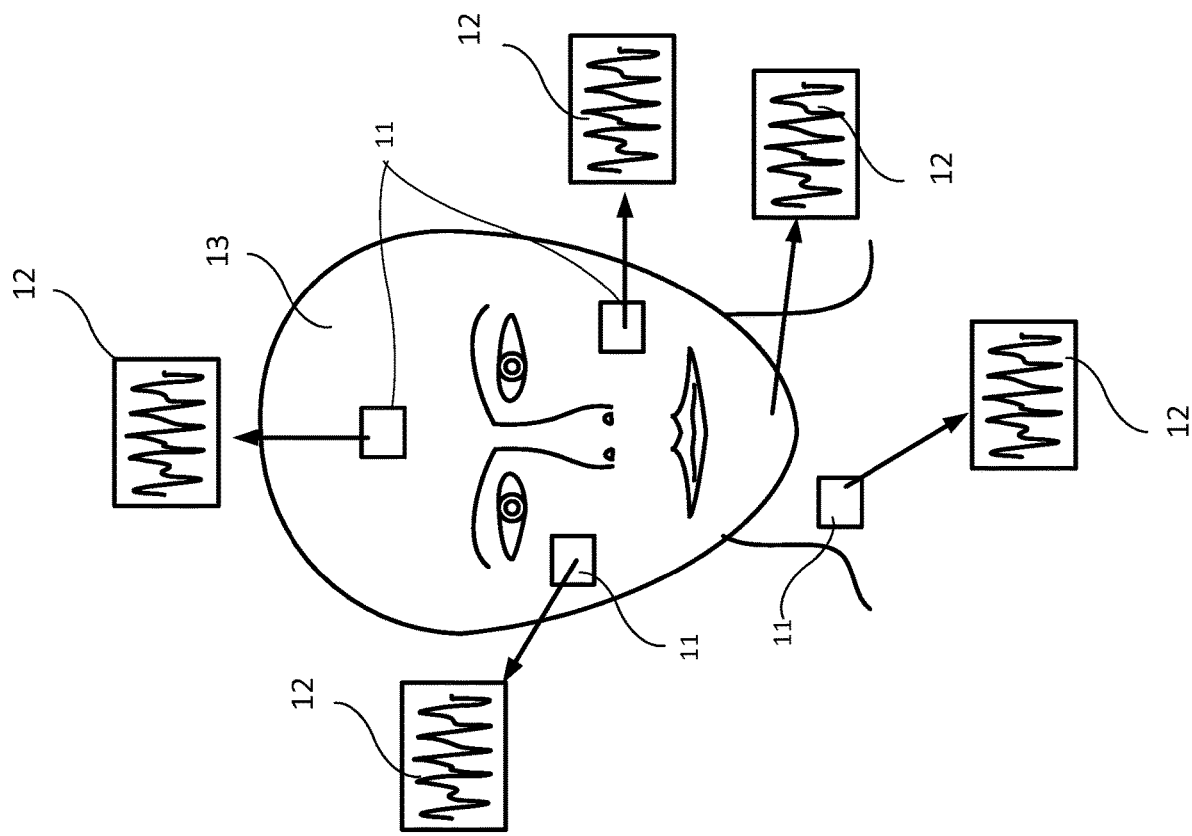
FIG. 4 shows a face with selected regions of interest.

Reference is now made to FIG. 4 which schematically shows a face 13 which has be captured over a series of images. There are a number of regions of interest 11 on the face. For each of these regions, the heart rate 12 is determined.

Figure 2:
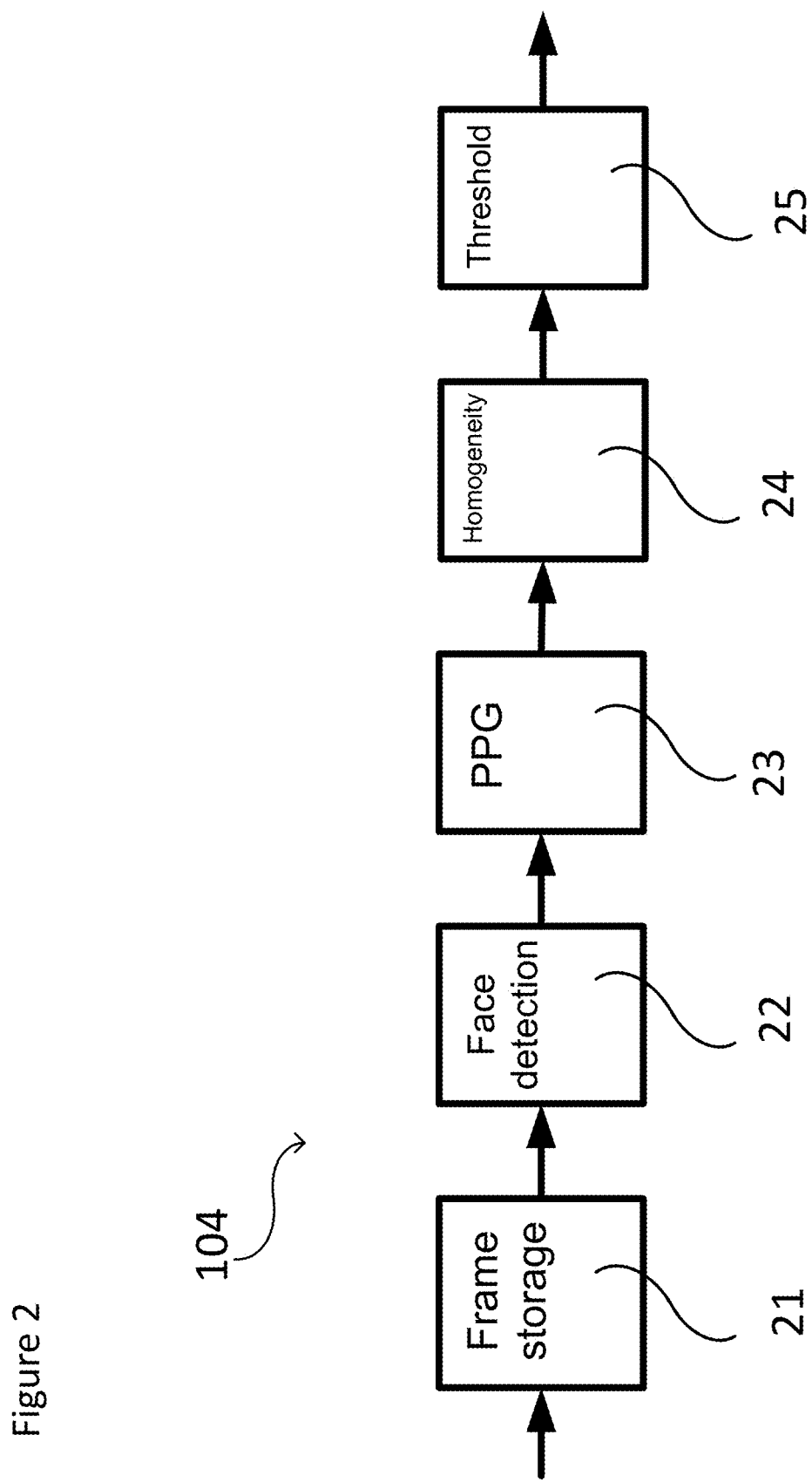
FIG. 2 shows schematically shows functional blocks of the signal processor of FIG. 1.
Figure 3:
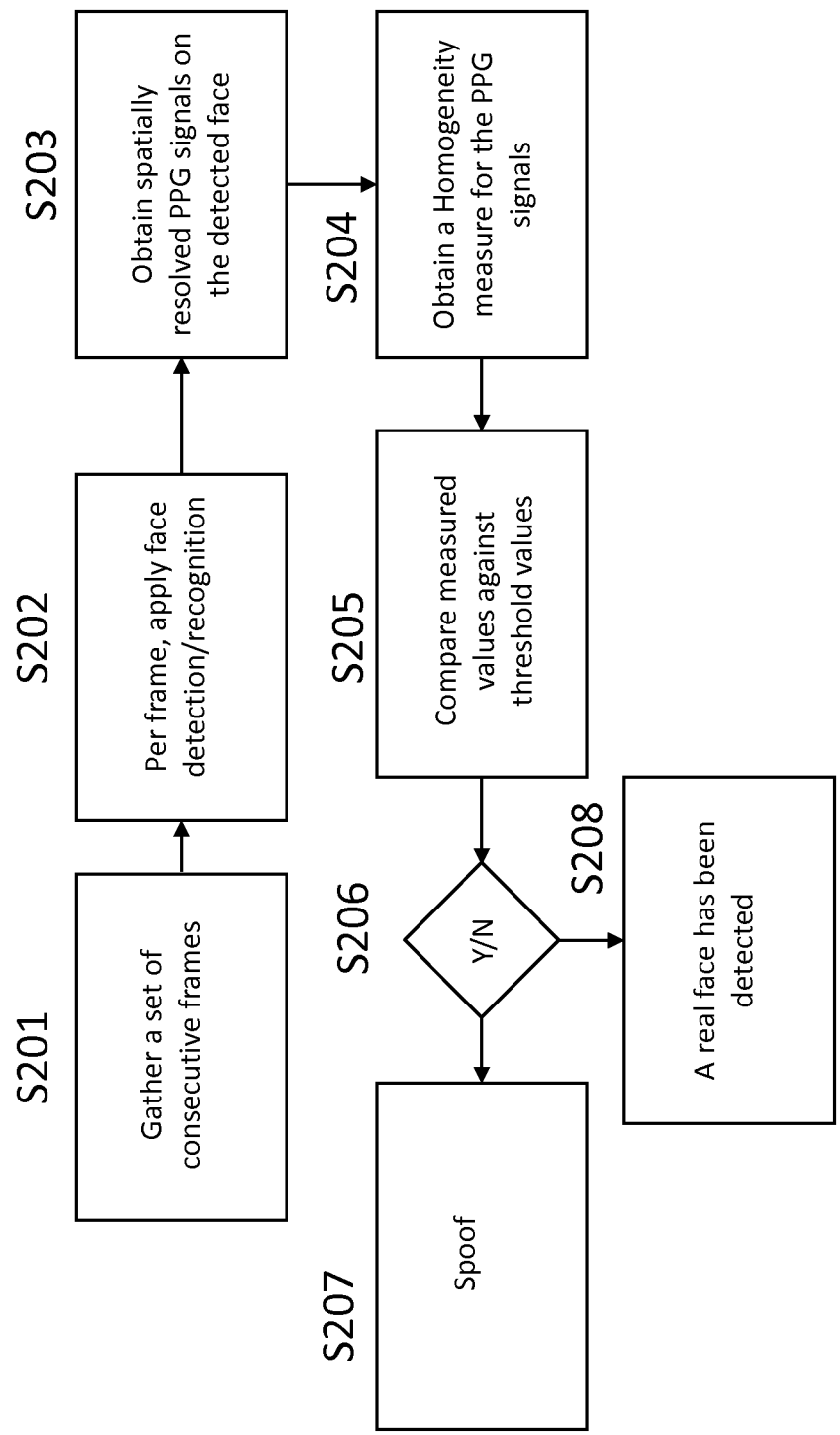
FIG. 3 shows a method of some embodiments.

Reference is now made to FIG. 2 which schematically shows functional blocks of the signal processor. This will be described in conjunction with FIG. 3 which shows the method of some embodiments.

In step S201 the camera captures a set of consecutive frames which are stored in memory for processing. Function block 21 causes the set of frames to be stored in memory. In some embodiments the set of consecutive frames may be temporally spread over a given period. The given period may be any suitable length of time. For example the period may be a 2 second period. In some embodiments the frames may be sampled at any suitable frequency, for example 7 Hz or a similar frequency. In some embodiments a time period of 2 seconds may be used to cover the frequency range of a human heart-rate (for example, 0.5 Hz-3.5 Hz). In some embodiments a 7 Hz sampling rate may be used to respect the Nyquist sampling theorem.

In step S202 on a per frame basis, a face detection or recognition algorithm is applied. This is performed by the face detection function block 22. In some embodiments, this step is performed to give a region of interest containing a face candidate on which the following part of the processing is operated. This is the face 13 shown in FIG. 4.

In step S203 spatially resolved photo-plethysmography (PPG) signals with respect to the detected face are obtained. This is performed by the photo-plethysmography function block 23. In some embodiments to obtain spatially resolved photo-plethysmographic waveforms, the face region may be divided into small sub-parts (for example, squares of 10×10 pixels) and processed to extract a waveform from each sub-part. These are the smaller regions of interest shown in FIG. 4. The photo-plethysmographic waveforms are referenced 12 in FIG. 4.

In step S204 a homogeneity measure for the PPG signals is obtained. This is performed by the homogeneity block 24. In some embodiments, once the waveforms are extracted a homogeneity measure may be computed. In some embodiments the homogeneity measure allows the waveforms to be verified as having the same characteristics.

The homogeneity measure may be derived in one or more of the following ways:

a. In some embodiments from each waveform the heart rate is extracted using Fourier Transform. Then the homogeneity measure H is calculated as:

$$H1 = \text{standard deviation}(all\_HR\_extracted) \quad (Eq.1)$$

b. In some embodiments from each waveform the heart rate is extracted using Fourier Transform. A histogram of the HR extracted is build and normalized. The homogeneity measure is then defined as:

$$H2 = \max(\text{Histo}(all\_HR\_extracted)) \quad (Eq.2)$$

c. In some embodiments all the waveforms are correlated (one with all others) to build a correlation matrix C. The homogeneity measure is then defined as:

$$H3 = \text{mean}(C\_Significant) \quad (Eq.3)$$

where C_Significant represents all correlation C with a p-value below a predetermined threshold.

d. In some embodiments waveforms are subdivided in multiple (possibly overlapping) time intervals, where for each time interval the HR is extracted. For example, to calculate the variation of the HR over time (temporal consistency) the standard deviation of the HR values can be calculated:

$$H4 = \text{standard deviation}(consecutive\_HR\_extracted) \quad (Eq.4)$$

e. In some embodiments for the HR values of the time intervals that were derived under d), the direction (vector) in 3D RGB (red/green/blue) colour space is calculated of the HR-related colour variation (HR-axis). For example, the variation of this direction (vector) over time (temporal consistency) can be calculated. For example, a method for doing this may be to first calculate the mean of the directions (vectors). The average (Euclidean) distance of the individual vectors to this mean vector may then expresses the variation. The difference of the variation in observed light spectrum to the expected heart-rate induced variation in the light spectrum (reference HR vector in colour space based on absorption spectrum of haemoglobin) may alternatively or additionally be used.

$$H5 = \text{mean}(\text{dist}(consecutive\_HR\_RGB\_vectors\text{-}mean(consecutive\_HR\_RGB\_vectors))) \quad (Eq.5)$$

In step S205 it is determined whether the measured PPG signals are greater than those of threshold values. This is performed by the threshold block 25. In some embodiments there is checking if the homogeneity measure is above or below a pre-determined threshold value T. For example, if the measured value is found to be above the threshold value, the face contained in the region of interest is qualified as "real-face".

In step S206, it is determined whether the detected signals meet the threshold criteria and a decision is made. This is performed by the threshold block 25.

In step S207, it is determined that the detected face is a spoof. This is performed by the threshold block 25.

In step S208, it is determined that the detected face is a real face. This is performed by the threshold block 25.

A suitable output may be provided depending on the determination made in step S206. For example a visual and/or audible alarm may be provided. In some embodiments, the output may be a control output which may be to open a gate or door if it determined that the detected face is a real face.

In some embodiments, a facial recognition algorithm may also be performed. The facial recognition algorithm may only be passed if it is determined that the detected face is a real face.

In some embodiments, heart rate related properties may be calculated and used as feature values. This may be in addition or as an alternative to the homogeneity value. For example: the (relative) amplitude of the pulse variation; the temporal shape of the pulses; and/or the presence in the frequency spectrum of higher harmonics of the fundamental pulse frequency may be used.

In some embodiments to reduce the effect that the variation in environmental light has in distorting the extracted heart rate (HR) signal, a combination of light sources may be added illuminating the human face. For example, these light sources may generate a diffuse, uniformly spatially distributed, and evenly distributed over the range of spectral sensitivity of the camera.

In some embodiments to improve the spatial homogeneity of the heart rate (HR) over the face, the amount of specular reflection from the skin may be reduced. This may be achieved for example where the detected light is cross-polarized. A polarizer may be placed in-front of the light source, and another polarizer may be placed in-front of the camera, the polarization direction of both polarizers may be chosen such that they are orthogonal with respect to each other.

In some embodiments infrared light may be used for illumination of the subject. The camera sensitivity may be in the infrared spectrum. These embodiments may make the detection less obtrusive.

In other embodiments other known techniques for signal extraction of the heart pulse may be utilized, for example, techniques which rely on small motions of the face (cardio-ballistography).

In some embodiments techniques such as Principal Component Analysis (PCA) and Independent Component Analysis (ICA) may be used. Other techniques that may be used include decomposition of the pulse component from the detected signals.

Both the (partial) motion of the human face as well as variations in the environmental light will distort the spatial and temporal homogeneity measures. In some embodiments the detector may measure and quantify both motion and light variation of the subject. In some embodiments, the detection decision in step S206 may be disabled if motion and/or light variation exceeds predefined values. Alternatively, the threshold levels for the homogeneity measures may be altered. For example a detection decision may be more relaxed in case of increasing amounts of motion and/or light variation.

In some embodiments instead of basing homogeneity measure H3 on correlation matrix calculated from the waveforms, the following may be considered for checking if the waveforms of regions are time aligned. For each signal the phase of the dominant frequency may be calculated. For a real face the phase values may only differ marginally over the face area. In some embodiments, the signals for different block sizes (scales) may be calculated. The dominant frequency for a block for a certain scale may be close to the dominant frequency of an overlapping larger block (at a higher scale), this may indicate that the signals of neighbouring blocks at a single scale are both time and frequency aligned.

In some embodiments, instead of comparing the homogeneity feature values H1 to H5 with a predefined threshold value individually, a classifier may be used to take the decision if a real face is present. The classifier may take the set of feature values as input, and take the classification decision based on determining the probability that the set of feature values may occur for a real face. By observing the feature values in combination, the classification decision may be made more accurately than observing each feature value individually.

In some embodiments two or more homogeneity metrics may be combined spatially and/or temporally.

In some embodiments the homogeneity value for time correlation H3 may be between each pair of signals. In some embodiments only sufficiently reliable homogeneity values may be used. This homogeneity value may be from a correlation of phases between the signals rather than a constant phase. A constant phase may be easier to spoof and in practice the HR varies over time.

In some embodiments the homogeneity value H4 may be for a total measurement period and may be subdivided into overlapping time intervals. The HR may be calculated for each interval. The variation of the HR may then be analysed over all time. If the face being measured is from a mask, the method used to generate H4 may give random values with a large spread. If the face being measured is real, the method used to generate H4 may give a far lower spread.

In some embodiments the homogeneity value H5 may be for direction in colour space, for example this may be 3D colour space (e.g. RGB—red/green/blue). In some embodiments the variation for the HR may be investigated in for example the red axis over time. Compare to expected variation from absorption of $HbO_2$ i.e. colour errors. From the haemoglobin absorption spectra one can expect to extract the "heart-beat" vector moving along specific direction in the RGB colour space. If variations are detected but do not correspond to the expected directions in colour space, the likelihood of spoofing is increased.

In other embodiments, the homogeneity value H5 may not be limited to 3D colour space, for example using a hyperspectral camera. For a real face the variation in reflected light spectrum may match the absorption spectrum of haemoglobin (after correction for spectrum of light source and for skin pigmentation), if the difference between both spectra is too large spoofing may be assumed.

Homogeneity values H1-H5 may be more appropriate when detecting different spoofing methods. For example values H1-H4 may be particularly useful to detect a mask, whereas H5 may be particularly useful to detect a varying light signal.

As the homogeneity values H1, and H2 are correlated, in some embodiments the system can chose between using either.

In some embodiments all the aforementioned techniques may be utilized. In others, two or more of the above mentioned techniques may be used.

It should be appreciated that the one or more techniques selected may be dependent on the application.

In some embodiments a face detection algorithm may be taught or trained to detect a real face by showing the system one or more real faces, and one or more fake faces.

In some embodiments the face detection algorithm may be taught or trained to weight the homogeneity values against a neural network decision or a support vector machine.

In some embodiments the face detection algorithm may utilize a comparison of a currently measured set of homogeneity values against previously measured homogeneity values.

In some embodiments the face detection algorithm may utilize a classification system of the homogeneity values.

In some embodiments any body areas/parts may be used to detect vital signs.

In some embodiments the vital sign used to determine whether a face is real may be a person's breathing motion.

Figure 5:
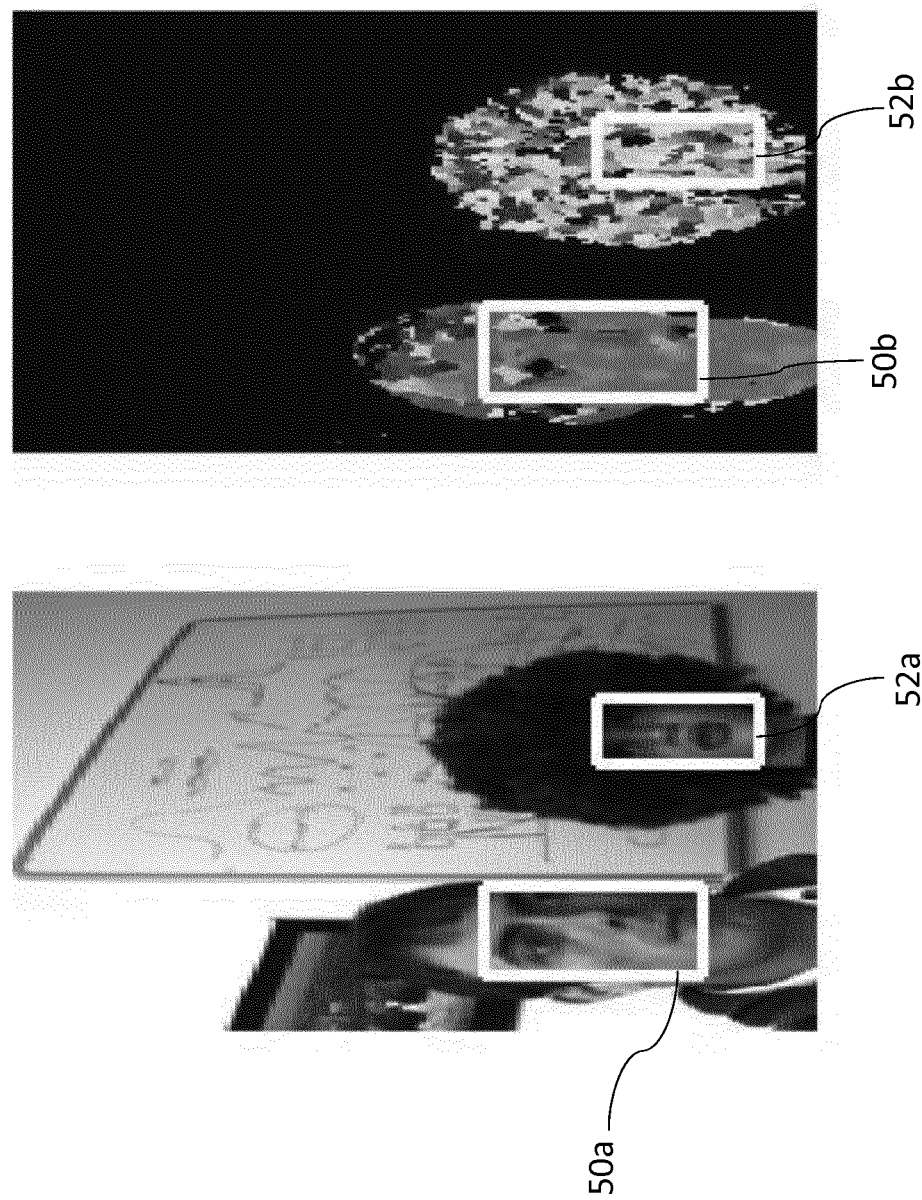
FIG. 5 shows selected faces in an image and a corresponding heart rate map.

Reference is made to FIG. 5 which shows on the left an image of two faces. The image referenced 50a is a real face and the image referenced 52a is that of a dummy made of plastic. The image on the right shows a respective HR map 50b and 52b for the two images.

The standard deviation and maximum may be taken from the face as a whole in homogeneity values H1 and H2. If the face is real, the histogram distribution will be narrow with a strong peak. If the face is a mask or a photo, frequencies would be randomly and evenly distributed over the histogram.

Correlation between waveform signals from different areas of the face may detect partial masks. This may additionally or alternatively help with illumination issues.

The colour vector method disclosed earlier allows the detection of spoofer sending a signal to simulate a heartbeat.

Consider the following analysis of this data using standard deviation.

From the heart-rate map of FIG. 5, the standard deviation is calculated for each rectangle and the homogeneity measure (according to Eq. 1) is calculated, leading to:

$H\_face\_left=10$ bpm;

$H\_face\_right=45$ bpm;

Setting the threshold value (T) to 20 ensures that the face on the right, the dummy face, is rejected.

Figure 6:
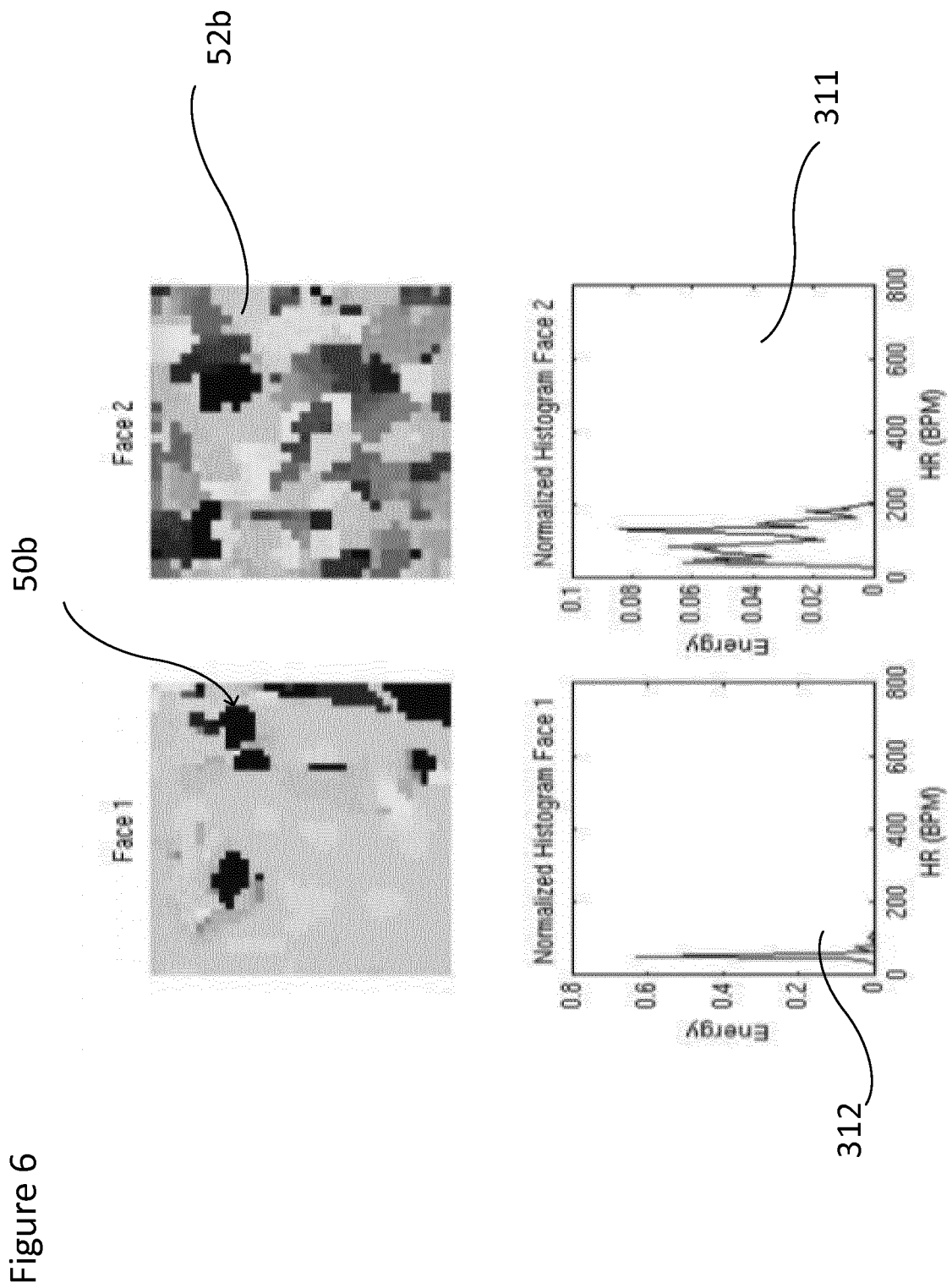
FIG. 6 shows in more detail the respective heart rate maps and associated histograms.

Consider the following analysis of this data using energy contained in the histogram. Reference is made to FIG. 6 which shows the image referenced 50b and the corresponding histogram 312 of heart rate against energy as well as the image reference 52b and the corresponding histogram 311. From the heart-rate map of FIG. 5 or 6, the histogram of heart-rate values may be computed for each rectangle and the homogeneity measure (according to Eq.2) may be calculated:

$H\_face\_left=0.6$;

$H\_face\_right=0.084$;

The histogram's peak originating from the left rectangle (real face) contains more energy compared to the histogram's peak originating from the right rectangle (dummy face). It should be noted that the energy axis of the two histograms have different scales.

Setting the threshold value (T) to 0.5 ensures that the face on the right, the dummy face, is rejected.

Consider the following analysis of this data using correlation of temporal signals. The detected waveforms from the left rectangle (real face) are correlated (one with all others); the same process may be applied for the right rectangle (dummy face). The homogeneity measure (according to Eq.3) may be extracted for each rectangle:

$H\_face\_left=0.79;$ $H\_face\_right=0.39;$

Setting the threshold value (T) to 0.5 ensures that the face on the right, the dummy face, is rejected.

Figure 7:
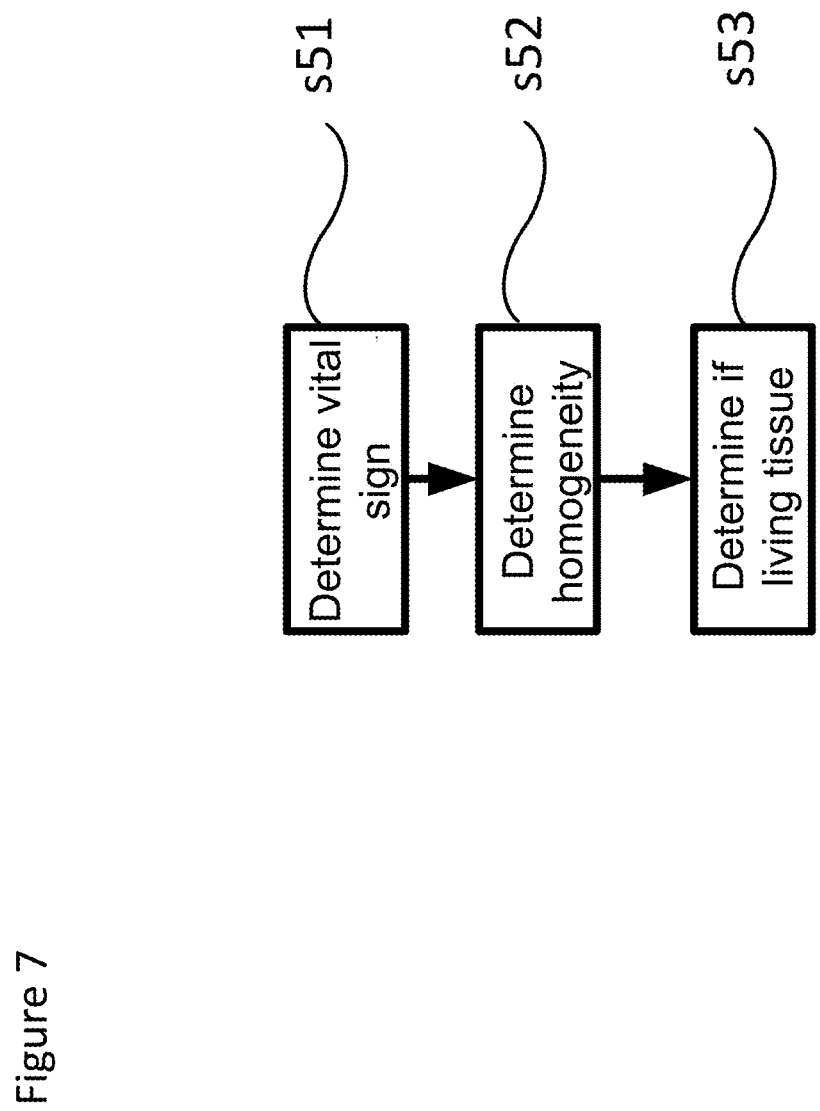
FIG. 7 shows a method of some embodiments.

Reference is now made to FIG. 7 which shows an embodiment of the present method for verifying whether a face is real.

In step S51, it is determined for a plurality of spatially separated regions of a surface, a respective measure of at least one vital sign.

In step S52, it is determined from the respective measures of said at least one vital sign, homogeneity information associated with the respective measures In step S53, the homogeneity information is used to determine if said spatially separate regions of said surface are living tissue.

Embodiments have many applications. For example, some embodiments may have application in the high security sector. Other embodiments may have application in consumer computer applications where a biometrics input is required.

Some embodiments may be used where identification of a person is based on face recognition using a camera. For example, some embodiments may provide authentication for logging into a smartphone using face recognition, or verification of a person's identification at an airport terminal through computerised means.

Some embodiments may be used for non-facial biometric recognition techniques, for example, finger print, or palm print recognition.

Aspects of the embodiments may be implemented in a computer program product, which may be a collection of computer program instructions stored on a computer readable storage device which may be executed by a computer. The instructions may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

Storage media suitable for storing computer program instructions include all forms of non-volatile memory, including but not limited to EPROM, EEPROM and flash memory devices, magnetic disks such as the internal and external hard disk drives, removable disks and CD-ROM disks. The computer program product may be distributed on such a storage medium, or may be offered for download through HTTP, FTP, email or through a server connected to a network such as the Internet.

Various embodiments with different variations have been described here above. It should be noted that those skilled in the art may combine various elements of these various embodiments and variations.

Such alterations, modifications, and improvements are intended to be part of this disclosure, and are intended to be within the scope of the present invention. Accordingly, the foregoing description is by way of example only and is not intended to be limiting. The present invention is limited only as defined in the following claims and the equivalents thereto.

The invention claimed is:

1. A computer implemented method comprising:
   determining respective measures of at least one vital sign for a plurality of spatially separated regions of a surface using at least one image;
   determining, from the respective measures of the at least one vital sign, homogeneity information associated with the respective measures; and
   determining when the spatially separate regions of the surface are living tissue based on the determined homogeneity information.

2. The method as claimed in claim 1, wherein the at least one image comprises a sequence of video frames, the method further comprising identifying a face area in the sequence of video frames, wherein at least one of the plurality of spatially separated regions is positioned in the face area, and the surface comprises at least partially the face area.

3. The method as claimed in claim 2, wherein the at least one vital sign comprises a heart-beat signal, said method further comprising extracting, from the sequence of video frames, a heart-beat signal for each of the spatially separated regions so as to obtain a plurality of heart-beat signals.

4. The method as claimed in claim 3, wherein determining the homogeneity information comprises comparing the heart-beat signals.

5. The method as claimed in claim 3, wherein determining the homogeneity information comprises extracting a heart-rate from the heart-beat signals for each of the plurality of spatially separate regions combining the extracted heart-rates from the plurality of the spatially separate regions, and determining at least one of a standard deviation and a maximum value of the combined heart-rates.

6. The method as claimed in claim 3, wherein determining the homogeneity information comprises finding a correlation between at least one pair of the heart-beat signals.

7. The method as claimed in claim 3, wherein determining the homogeneity information comprises extracting heart-rates from a plurality of time segments of a spatially separate region of the plurality of spatially separate regions and determining a standard deviation of the heart-rates extracted from each time segment.

8. The method as claimed in claim 3, further comprising determining an area in the sequence of video frames where respiration is measurable, extracting a respiration signal from the determined area, extracting a correlation between the extracted respiration signal and the heart-beat signal, and comparing the correlation to a limit.

9. The method as claimed in claim 1, wherein determining when the spatially separate regions of the surface are living tissue comprises comparing said homogeneity information against a limit.

10. The method as claimed in claim 1, further comprising determining a colour vector for each of a plurality of time segments of a spatially separate region of the plurality of spatially separate regions and determining variations of the colour vectors over the plurality of time segments.

11. The method as claimed in claim 10, wherein the colour vector is obtained from a haemoglobin absorption spectrum.

12. A spoofing detection apparatus comprising
    at least one processor; and
    a non-transitory memory for storing instructions that when executed by the at least one processor, cause the at least one processor to:

determine respective measures of at least one vital sign for a plurality of spatially separated regions of a surface;

determine from the respective measures of the at least one vital sign homogeneity information associated with the respective measures; and determine when the spatially separate regions of the surface are living tissue based on the homogeneity information.

13. The spoofing detection apparatus of claim 12, further comprising:

an input to receive a sequence of video frames, wherein the instructins further cause the at least one processor to, identify a face area in the sequence of video frames, identify spatially separate skin portions in the face area as the plurality of spatially separated regions of the surface, extract a heart-beat signal for each of the spatially separate skin portions, and to extract a heart-rate from each heart-beat signal.

14. The spoofing detection apparatus of claim 13, wherein the instructions further cause the at least one processor to calculate a valid vital sign metric and compare the calculated valid vital sign metric against a limit to decide if the sequence of video frames containing the face area has been captured directly from the face of a living person.

* * * * *